(12) United States Patent
Davis (10) Patent No.: US 11,445,893 B2
(45) Date of Patent: Sep. 20, 2022

(54) MEDICAL DEVICE CONNECTION MEMBER

(71) Applicant: BOSTON SCIENTIFIC SCIMED, INC., Maple Grove, MN (US)

(72) Inventor: Scott A. Davis, Southborough, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 298 days.

(21) Appl. No.: 16/235,820

(22) Filed: Dec. 28, 2018

(65) Prior Publication Data

US 2019/0208994 A1 Jul. 11, 2019

Related U.S. Application Data

(60) Provisional application No. 62/613,810, filed on Jan. 5, 2018.

(51) Int. Cl.
| | | |
|---|---|---|
| *A61B 1/00* | (2006.01) | |
| *A61B 1/005* | (2006.01) | |
| *A61B 34/00* | (2016.01) | |

(52) U.S. Cl.
CPC ........ *A61B 1/00128* (2013.01); *A61B 1/0057* (2013.01); *A61B 1/00085* (2013.01); *A61B 1/00087* (2013.01); *A61B 1/00133* (2013.01); *A61B 34/70* (2016.02)

(58) Field of Classification Search
CPC .. F16B 7/182; F16B 7/187; F16B 7/20; F16B 7/22; A61B 2014/2931; A61B 2014/294; A61B 1/00128; A61B 1/00133; A61B 1/00087; A61B 1/00085; A61B 1/00112; A61B 1/00121
See application file for complete search history.

(56) References Cited

U.S. PATENT DOCUMENTS

| | | | |
|---|---|---|---|
| 4,886,304 A * | 12/1989 | Kunsman | F16L 19/065 285/104 |
| 7,367,973 B2 | 5/2008 | Manzo et al. | |
| 8,764,735 B2 | 7/2014 | Coe et al. | |
| 8,998,939 B2 * | 4/2015 | Price | A61B 18/1442 606/169 |
| 9,125,681 B2 | 9/2015 | Parihar et al. | |
| 2006/0184161 A1 | 8/2006 | Maahs et al. | |
| 2007/0073247 A1 | 3/2007 | Ewaschuk | |
| 2012/0078291 A1 | 3/2012 | Nobis et al. | |
| 2012/0289773 A1 | 11/2012 | Joshi et al. | |
| 2016/0213387 A1 * | 7/2016 | DeGraaf | A61B 1/018 |

FOREIGN PATENT DOCUMENTS

EP 1561413 A1 * 8/2005 ............. A61B 17/29

* cited by examiner

*Primary Examiner* — Sarah A Simpson
(74) *Attorney, Agent, or Firm* — Seager, Tufte & Wickhem, LLP (57) ABSTRACT

An example medical device is disclosed. The example medical device includes an elongate member having proximal end region and a distal end region. The medical device also includes an end effector having a proximal end region and a distal end region. Additionally, the medical device includes a connection member coupled to the distal end region of the elongate member and the proximal end region of the end effector, the connection member having a first outer surface and a first outer diameter. The medical device also includes a first bushing positioned adjacent to the connection member, the first bushing having a second outer surface and a second outer diameter larger than the first outer diameter.

17 Claims, 6 Drawing Sheets

MEDICAL DEVICE CONNECTION MEMBER

CROSS-REFERENCE TO RELATED APPLICATIONS

This application claims priority under 35 U.S.C. § 119 to U.S. Provisional Application Ser. No. 62/613,810, filed Jan. 5, 2018, the entirety of which is incorporated herein by reference.

TECHNICAL FIELD

The present disclosure pertains to medical devices, and methods for manufacturing medical devices. More particularly, the present disclosure pertains to medical devices including a connection member which reduces frictional forces within the medical device.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device includes an elongate member having proximal end region and a distal end region. The medical device also includes an end effector having a proximal end region and a distal end region. Additionally, the medical device includes a connection member coupled to the distal end region of the elongate member and the proximal end region of the end effector, the connection member having a first outer surface and a first outer diameter. The medical device also includes a first bushing positioned adjacent to the connection member, the first bushing having a second outer surface and a second outer diameter larger than the first outer diameter.

Alternatively or additionally to any of the embodiments above, further comprising an outer catheter having a proximal end region, a distal end region and a lumen extending therein, wherein the elongate member is configured to translate, rotate or both translate and rotate within at least a portion of the lumen of the outer catheter.

Alternatively or additionally to any of the embodiments above, wherein the outer catheter includes an inner surface, and wherein the second outer surface of the first bushing is configured to shield the first outer surface of the connection member from contact with inner surface of the outer catheter.

Alternatively or additionally to any of the embodiments above, wherein the bushing includes an aperture, and wherein the elongate member extends through the aperture.

Alternatively or additionally to any of the embodiments above, wherein the bushing is rigidly attached to the elongate member.

Alternatively or additionally to any of the embodiments above, wherein the bushing is free to translate, rotate or both translate and rotate along the elongate member.

Alternatively or additionally to any of the embodiments above, wherein the bushing extends circumferentially around an outer surface of the elongate member.

Alternatively or additionally to any of the embodiments above, wherein the bushing directly contacts the connection member.

Alternatively or additionally to any of the embodiments above, further comprising a second bushing, and wherein the first bushing is positioned proximal to the connection member and wherein the second bushing is positioned distal to the connection member.

Alternatively or additionally to any of the embodiments above, wherein the second bushing includes a third outer diameter and wherein the third outer diameter is greater than the first outer diameter.

Alternatively or additionally to any of the embodiments above, wherein the distal end region of the end effector includes a basket.

Alternatively or additionally to any of the embodiments above, wherein the distal end region of the end effector includes a snare.

Another example medical device, comprising:
a handle;
an outer member coupled to the handle, the outer tubular member having an inner surface and a lumen extending therein;
a drive shaft extending within the lumen of the outer member, the drive shaft having a proximal shaft portion and a distal shaft portion;
an end effector coupled to the distal shaft portion of the drive shaft; and
a connection system configured to couple the proximal shaft portion of the drive shaft to the distal shaft portion of the drive shaft;
wherein the connection system includes a connection member having a first outer diameter and a bushing having a second diameter larger than the first diameter.

Alternatively or additionally to any of the embodiments above, wherein the bushing is configured to space the outer surface of the connection member away from the inner surface of the outer member.

Alternatively or additionally to any of the embodiments above, wherein the bushing includes an aperture, and wherein the drive shaft extends through the aperture.

Alternatively or additionally to any of the embodiments above, wherein the bushing is rigidly attached to the drive shaft.

Alternatively or additionally to any of the embodiments above, wherein the bushing is free to translate, rotate or both translate and rotate along the drive shaft.

Alternatively or additionally to any of the embodiments above, wherein the bushing directly contacts the connection member.

Alternatively or additionally to any of the embodiments above, further comprising a second bushing, and wherein the first bushing is positioned proximal to the connection member and wherein the second bushing is positioned distal to the connection member.

An example endoscope, comprising:
a handle;
an outer member coupled to the handle, the outer tubular member having an inner surface and a lumen extending therein;

a drive shaft extending within the lumen of the outer member, the drive shaft having a proximal shaft portion and a distal shaft portion;

an end effector coupled to the distal shaft portion of the drive shaft;

a connection member having a first end attached to the proximal shaft portion and a second end attached to the distal shaft portion; and a spacing member positioned adjacent to the connection member;

wherein the spacing member is configured to prevent an outer surface of the connection member from contacting the inner surface of the outer member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Figure 1:
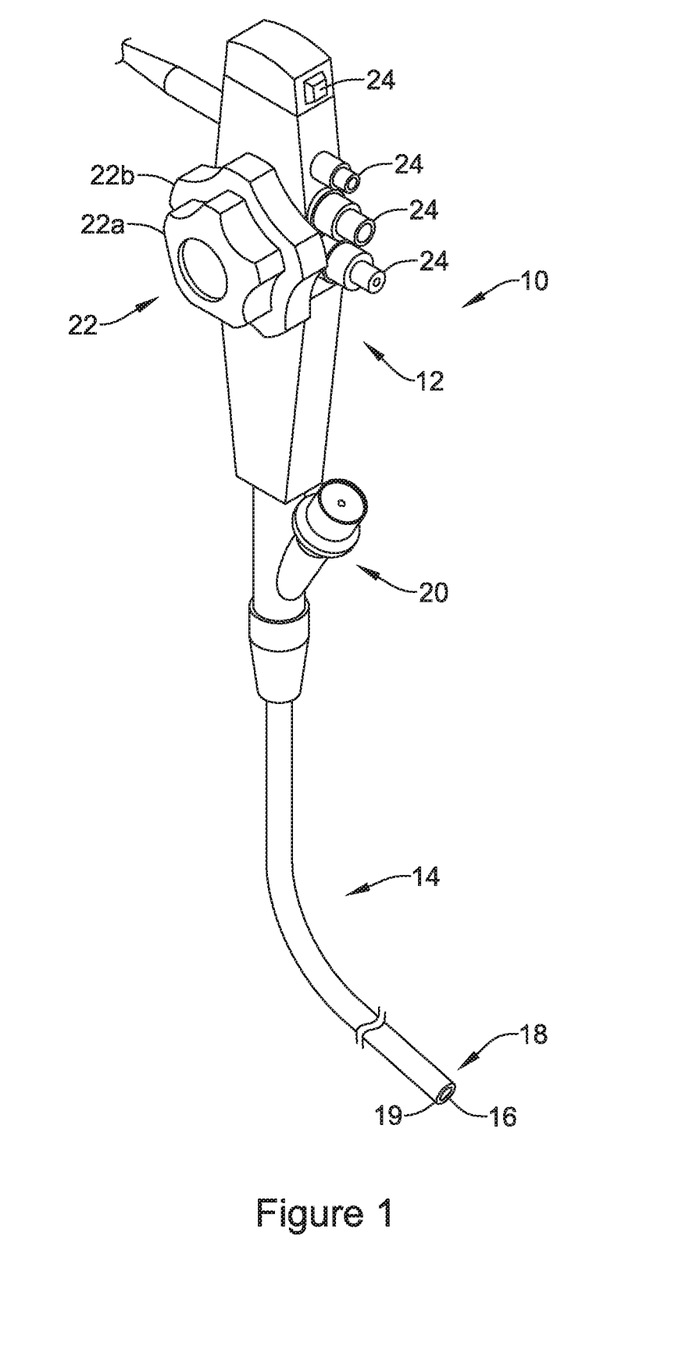
FIG. 1 is a perspective view of an example medical device.

FIG. 1 is a perspective view of an example medical device 10. The medical device 10 may be any of a number of different types of medical devices. The medical device 10 may be utilized in a variety of medical interventions. For example, medical device 10 may be an endoscope or similar device. The particular type of medical device 10 may be identified by the particular anatomy desired to be reached. For example, the medical device 10 may be a bronchoscope, colonoscope, duodenoscope, esophagoscope, guidetubes, introducers (without or without vision or visualization capabilities), or any other type of related medical device. The medical device 10 may include a handle 12 and an outer elongate shaft 14 extending distally from the handle 12 to a distal tip 18. In general, the outer shaft 14 may take the form of a polymer or metal tube. In some embodiments, the shaft 14 may be constructed with a reinforcing braid, liner, web, weave, etc.

Additionally, the shaft 14 may include a lumen defining a working channel 16 extending through the shaft 14 from a distal end region 19 near distal tip 18 of the shaft 14 to an access port 20 that may be positioned in the handle 12 or another portion of the medical device 10. Although the medical device 10 is depicted with a single working channel 16 in FIG. 1, it can be appreciated that in other embodiments, the medical device 10 may include multiple working channels, as desired.

The handle 12 may include one or a plurality of controls 22, such as rotating knobs, which may be used to control movement of the distal tip 18 of the shaft 14 during operation. For example, a first rotating knob 22a may control up and down movement or deflection of the distal tip 18 of the shaft 14, while a second rotating knob 22b may control side-to-side movement or deflection of the distal tip 18 of the shaft 14. The handle 12 may also include one or a plurality of buttons 24, which may be used to activate suction or deliver fluid such as air, saline and/or water, etc. through a lumen of the medical device 10 or perform other functions as desired. These are just examples. Other variations and/or feature for medical device 10 are contemplated.

Figure 2:
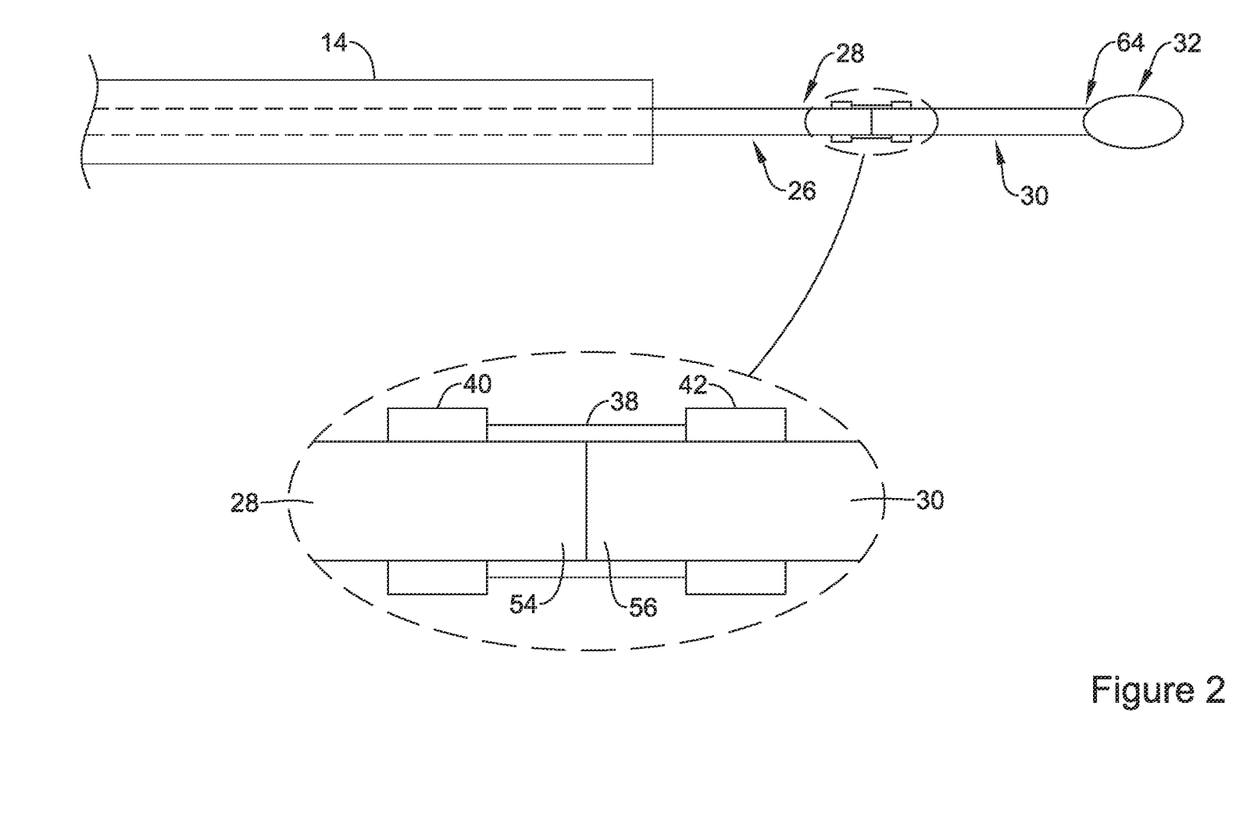
FIG. 2 is a side view of another example medical device.

FIG. 2 illustrates a portion of the outer shaft 14 shown in FIG. 1. Additionally, FIG. 2 shows that an inner elongate shaft 26 that may be slidably disposed within at least a portion of the working channel 16 of the shaft 14. The shaft 26 may take the form of a solid wire, multiple wires (in a straight or twisted configuration), a tube, a braid or multiple braided wires, or the like. In some examples, shaft 26 may be referred to as a drive shaft. The drive shaft 26 may translate and/or rotate within the working channel 16 of the outer shaft 14. In some examples, the handle 12 may be a mechanized (e.g., motorized) handle which translates and/or rotates the shaft 26.

The shaft 26 may include a proximal portion 28 and a distal portion 30. As discussed above, the proximal shaft portion 28 and/or the distal shaft portion 30 may take the form of a solid wire, multiple wires (in a straight or twisted configuration), a tube, a braid or multiple braided wires, or the like. In some examples, the proximal portion 28 may be separated (e.g., unattached) from the distal portion 30. Additionally, FIG. 2 illustrates that in some examples an end effector 32 may be coupled to a distal end region 64 of the distal shaft portion 30 of the shaft 26. The end effector 32 may include a variety of possible structures and/or configurations. For example, the end effector 32 may include a snare, basket, light, LED, needle, clevis, brush, tome, forceps, grasper, hemostatic clip, etc. These are just examples. It can be appreciated that different end effectors 32 may be utilized for specific medical interventions.

As will be described in greater detail below, the detailed view of FIG. 2 further illustrates that in some examples the proximal shaft portion 28 of the shaft 26 may be coupled to the distal shaft portion 30 of the shaft 26 via a connection member 38. In some examples the connection member 38 be a tubular member which includes a lumen (not shown in FIG. 2) extending therethrough. The connection member 38 may be designed to receive both the proximal shaft portion 28 and the distal shaft portion 30 of the shaft 26. In some examples, the connection member 38 may be designed to attach to both the proximal shaft portion 28 and the distal shaft portion 30 of the shaft 26, thereby rigidly coupling the proximal shaft portion 28 to the distal shaft portion 30 of the shaft 26. For example, the connection member 38 may be designed with a polymer material that shrinks down and fixedly secures onto both the proximal shaft portion 28 and the distal shaft portion 30 of the shaft 26.

As will be discussed in greater detail below, medical device 10 may include a first bushing 40 and/or a second bushing 42 positioned along the shaft 26. For simplicity purposes, both the bushing 40 and the bushing 42 are shown in FIG. 2, however, it is contemplated that in some examples the medical device 10 may include the first bushing 40, the second bushing 42 or both the first bushing 40 and the second bushing 42. Furthermore, as shown in FIG. 2, in some examples the first bushing 40 may be positioned proximal of the connection member 38 while the second bushing 42 may be positioned distal to the connection member 38. Additionally, in some examples, the first bushing 40, the second bushing 42 or both the first bushing 40 and the second bushing 42 may directly contact the connection member 38. However, in other examples it is contemplated that the first bushing 40, the second bushing 42 or both the first bushing 40 and the second bushing 42 may be spaced away from the connection member 38 along the longitudinal axis of the medical device 10.

Figure 3:
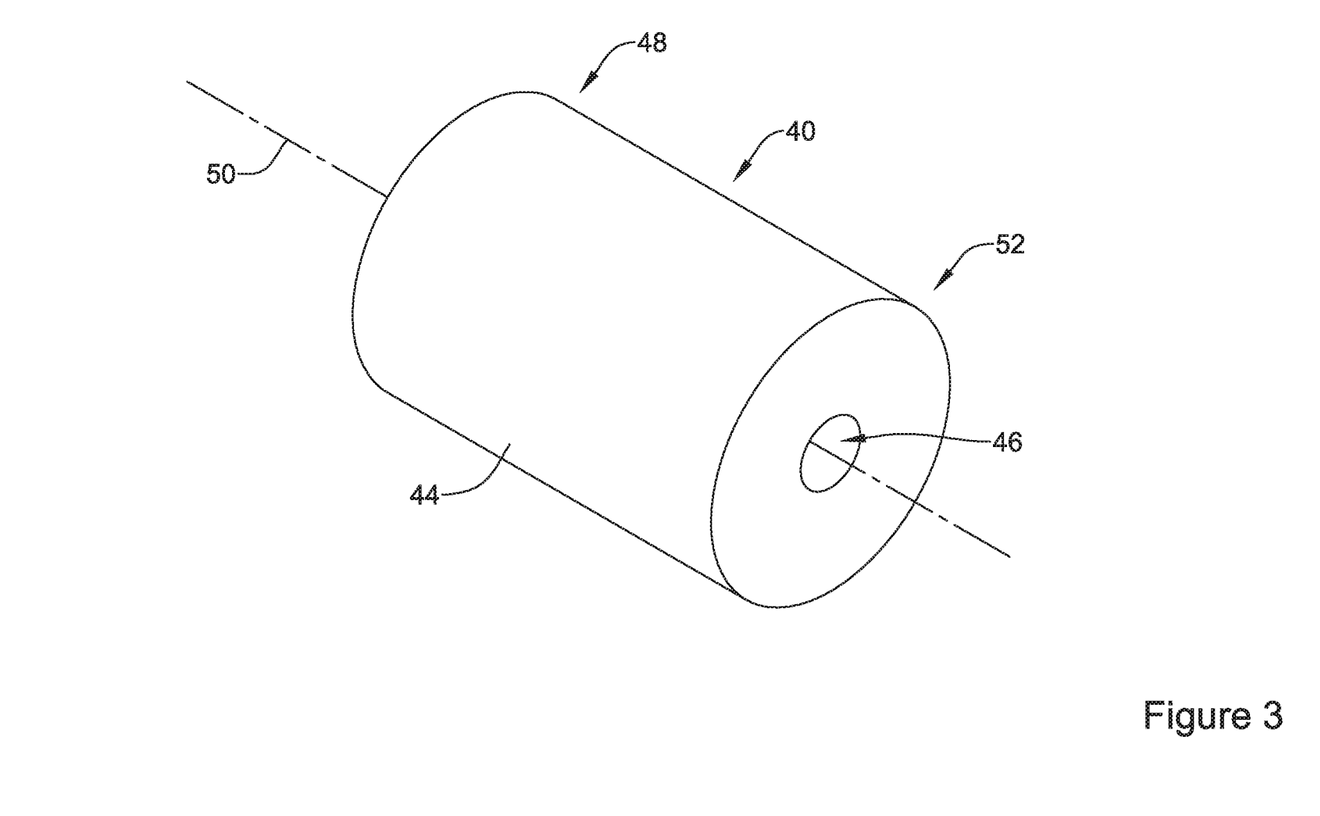
FIG. 3 illustrates a component of the medical device shown in FIG. 2.

FIG. 3 shows a perspective view of the first bushing 40 discussed above with respect to FIG. 2. As shown in FIG. 3, the first bushing 40 may be substantially cylindrical in shape and may include an outer surface 44 which extends circumferentially around the longitudinal axis 50 (depicted by the dashed line in FIG. 3) of the bushing 40. Additionally, the first bushing may include an aperture 46 extending from a first end 48 of the first bushing 40 to a second end 52 of the first bushing 40. It can be appreciated that shaft 26 (discussed above) may extend through the aperture 46 of the first bushing 40. While the following discussion relates to the first bushing 40, it can be appreciated that the second bushing 42 may include similar features and function in a similar manner to the first bushing. For example, the second bushing 42 may include an outer surface and an aperture extending therethrough. However, this is not intended to be limiting. Rather, in some examples the first bushing 40 and the second bushing 42 may be different in shape (e.g., width, length, etc.) from one another while still maintaining sufficient functionality.

Figure 4:
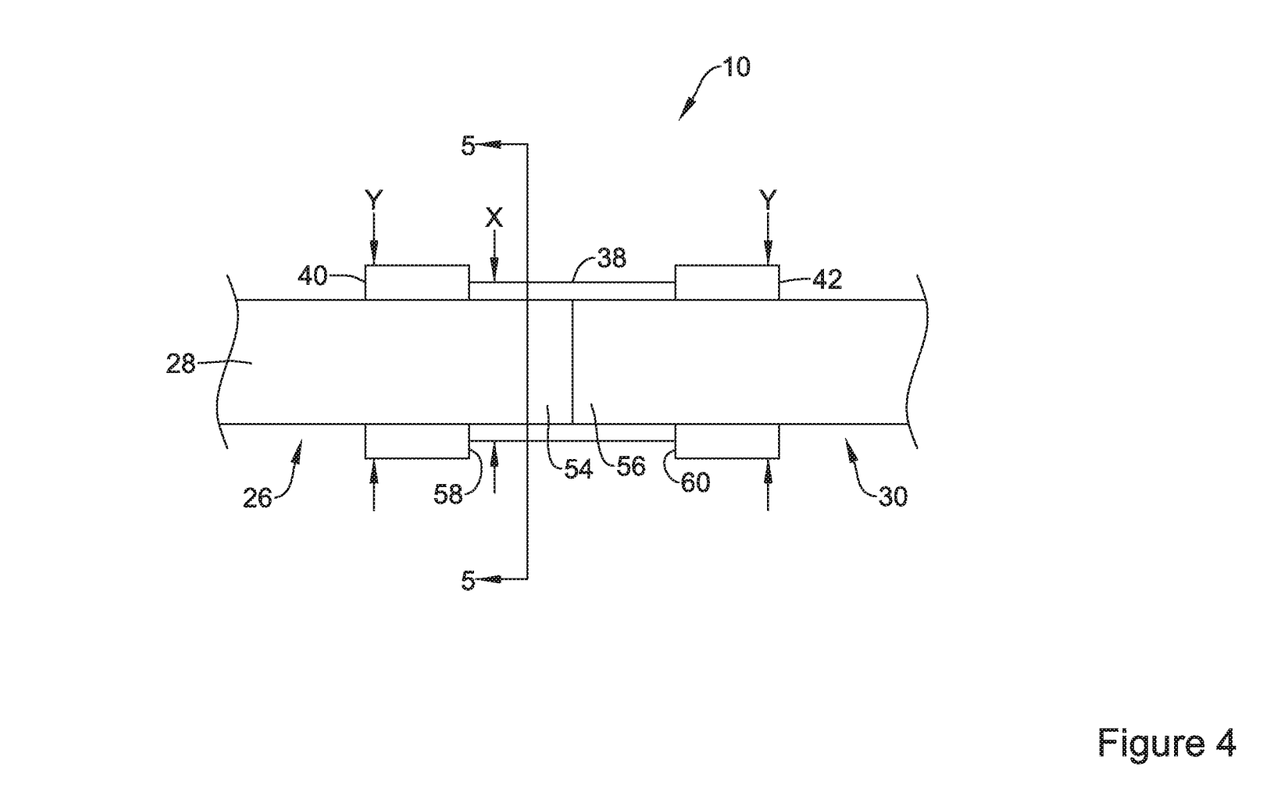
FIG. 4 illustrates a portion of the medical device shown in FIG. 2.

FIG. 4 illustrates a portion of the medical device 10 of FIG. 2. Specifically, FIG. 4 shows the shaft 26 including the proximal shaft portion 28 coupled to the distal shaft portion 30 via the connection member 38. Additionally, the FIG. 2 illustrates that the proximal shaft portion 28 includes a distal end 54 which may be inserted into a lumen of the connection member 38. Further, FIG. 4 illustrates that the distal shaft portion 30 includes a proximal end 56 which may be inserted into a lumen of the connection member 38. As illustrated in FIG. 4, the distal end 54 of the proximal shaft portion 28 may be positioned adjacent and/or abut the proximal end 56 of the distal shaft portion 30.

Additionally, FIG. 4 shows the first bushing 40 positioned along the proximal shaft portion 28 and the second bushing 42 positioned along the distal shaft portion 30. As illustrated in FIG. 4, a distal face 58 of the first bushing 40 may directly abut (e.g., contact) the connection member 38 while a proximal face 60 of the second bushing 42 may directly abut (e.g., contact) the connection member 38. It is contemplated that each of the first bushing 40 and the second bushing 42 may be positioned such that they contact, but are not directly attached, to the connection member 38. It can be appreciated that by not directly attaching the first bushing 40 and/or the second bushing 42 to the connection member 38 (and/or the proximal shaft portion 28 and distal shaft portion 30), a greater degree of flexibility may be imparted to that portion of the medical device 10. In other words, by not directly attaching the first bushing 40, the second bushing 42 and the connection member 38 to one another, each of the first bushing 40, the second bushing 42 and/or the connection member 38 may be able to shift relative to one another, thereby imparting a greater degree of flexibility to the medical device 10. However, this is not intended to be limiting. It is contemplated that in some examples, the first bushing 40, the second bushing 42 and/or the connection member 38 may be directly attached to one another and/or the proximal shaft portion 28 and the distal shaft portion 30.

FIG. 4 further illustrates that the first bushing 40 and/or the second bushing 42 may include an outer diameter depicted as dimension "Y" in FIG. 4. Additionally, FIG. 4 illustrates that the connection member 38 may include an outer diameter depicted as dimension "X" in FIG. 4. In some instances it may be desirable for the outer diameter of the first bushing 40 and the second bushing 42 to be greater than the diameter of the connection member 38. For example, in some instances the difference between dimension "Y" and dimension "X" may be about 0.0005" to 0.005", or about 0.0015" to 0.0035", or about 0.002" to about 0.003." It is further contemplated that in some instances the first bushing 40 may include an outer diameter that is different than the outer diameter of the second bushing 42, whereby both the diameter of the first bushing 40 and the second bushing 42 remain greater than the diameter of the connection member 38.

Figure 5:
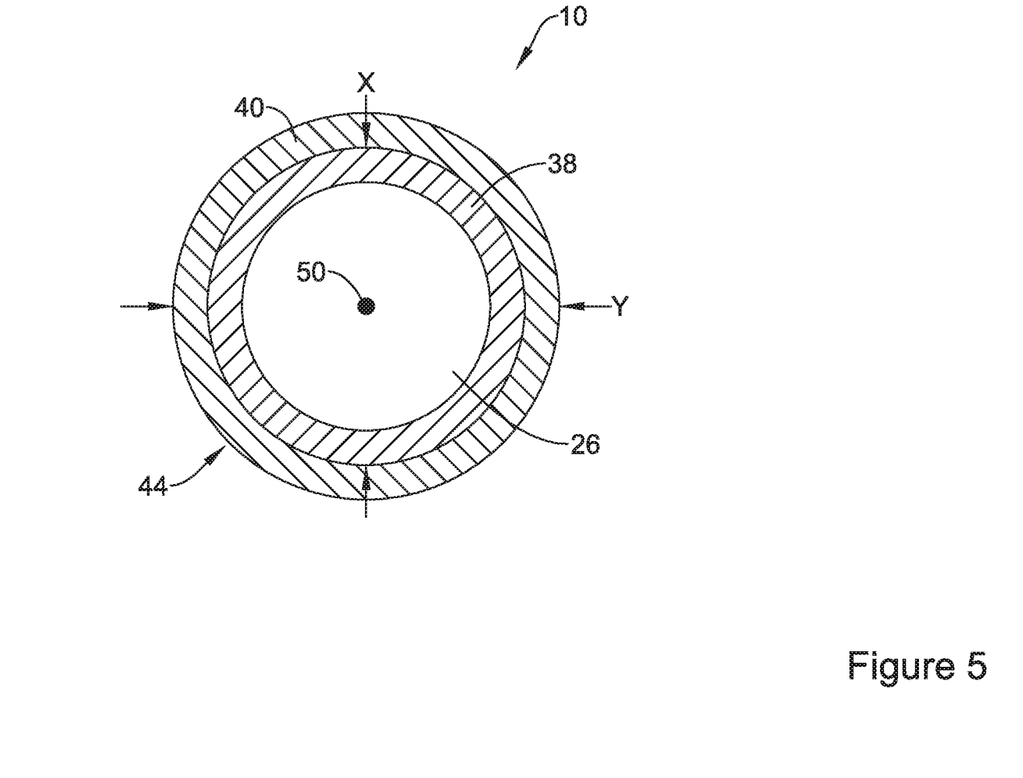
FIG. 5 is a cross-sectional view taken along line 5-5 of the example medical device shown in FIG. 4.

FIG. 5 is a cross-sectional view taken along line 5-5 of FIG. 4. FIG. 5 further illustrates the outer diameter of the first bushing 40 (depicted as dimension "Y") shown in FIG. 4. It is noted that the second bushing 42 is not shown in FIG. 5, but it can be appreciated that its outer diameter may be similar to that of the first bushing 40. Additionally, FIG. 5 illustrates that the connection member 38 may include an outer diameter depicted as dimension "X" and that dimension "Y" is greater than dimension "X." As discussed above, FIG. 5 illustrates that the first bushing 40 may extend circumferentially around the longitudinal axis 50 of the medical device 10.

Figure 6:
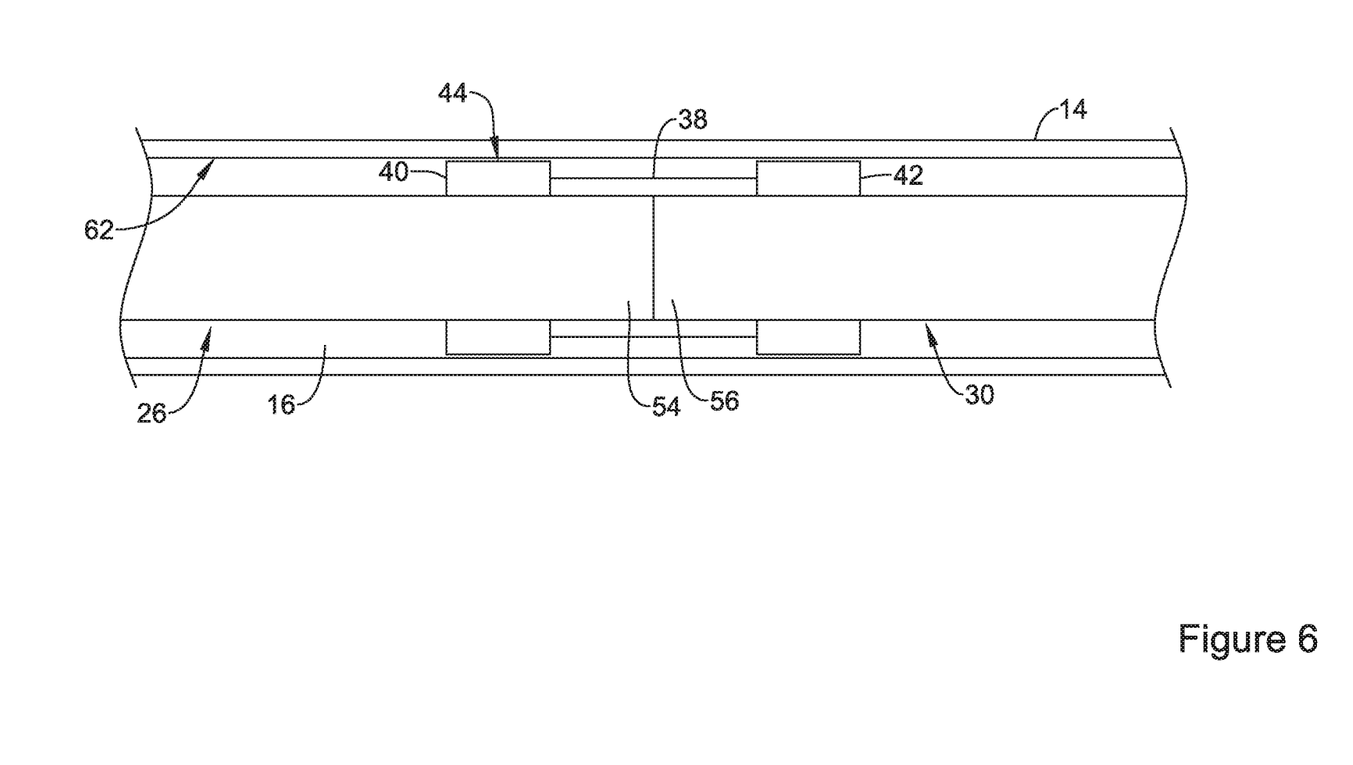
FIG. 6 is a side view of an example medical device positioned within a tubular member.

FIG. 6 illustrates the first bushing 40, the second bushing 42 and the connection member 38 positioned within the working channel 16 of the example tubular member 14 discussed above. It can be appreciated that the first bushing 40, the second bushing 42 and the connection member 38 may translate and/or rotate with the working channel 16 as the inner shaft 26 is translated and/or rotated within the outer shaft 14 (e.g., when the inner shaft 26 is translated relative to the outer shaft 14 upon deployment and/or retraction of an end effector as described above).

In some instances it may be beneficial to prevent the connection member 38 from coming into contact with the outer shaft 14 when the inner shaft 26 is being translated and/or rotated within the working channel 16 of the outer shaft 14. FIG. 6 illustrates that the first bushing 40 and/or the second bushing 42 may space the connection member 38 away from the inner surface 62 of the working channel 16 of the outer shaft 14. It can be appreciated that the larger diameter of the first bushing 40 and/or the second bushing 42 as compared to the diameter of the connection member 38 may permit the first bushing 40 and/or the second bushing 42 to shield the connection member 38 from coming into contact with the inner surface 62 of the working channel 16 as the inner shaft 26 translates and/or rotates with the working channel 16. Preventing the connection member 38 from contacting the inner surface 62 of the outer shaft 14 may reduce (or eliminate) the friction between the connection member 38 and the inner surface 62 of the outer shaft 14. Reducing the friction between a connecting member (e.g., connection member 38) and the tubular components within which the connection is positioned is desirable in any medical device, but may be particularly important in medical devices having relatively smaller lumen sizes. It can be appreciated that the first bushing 40 and/or the second bushing 42 may be designed from materials having low coefficients of friction. A non-limiting list of example materials that may be utilized for the construction of bushing 40 and/or bushing 42 are disclosed below.

The materials that can be used for the various components of assembly (and/or other assemblies disclosed herein) and the various tubular members disclosed herein may include those commonly associated with medical devices. For simplicity purposes, the following discussion makes reference to endoscopic instrument and other components of endoscope. However, this is not intended to limit the devices and methods described herein, as the discussion may be applied to other similar tubular members and/or components of tubular members or devices disclosed herein.

The medical device 10 and/or components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, endoscopic instrument and/or other portions of assembly may also be doped with, made of, or otherwise include a radiopaque material. Radiopaque materials are understood to be materials capable of producing a relatively bright image on a fluoroscopy screen or another imaging technique during a medical procedure. This relatively bright image aids the user of assembly in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of assembly to achieve the same result.

In some embodiments, a degree of Magnetic Resonance Imaging (Mill) compatibility is imparted into assembly. For example, assembly and/or endoscopic instrument, or portions thereof, may be made of a material that does not substantially distort the image and create substantial artifacts (e.g., gaps in the image). Certain ferromagnetic materials, for example, may not be suitable because they may create artifacts in an MRI image. Assembly and/or endoscopic instrument, or portions thereof, may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device, comprising:
an elongate member having a proximal end region and a distal end region;
an end effector having a proximal end region and a distal end region;
a connection member coupled to the distal end region of the elongate member and the proximal end region of the end effector, the connection member having a first outer surface, a first outer diameter, and an inner lumen;
a first bushing positioned adjacent to the connection member, the first bushing having a second outer surface and a second outer diameter larger than the first outer diameter, wherein the first bushing is directly attached and affixed relative to an outer surface of the elongate member;
wherein the distal end region of the elongate member extends within a portion of the inner lumen of the connection member;
wherein the proximal end region of the end effector extends within a portion of the inner lumen of the connection member;
wherein the first bushing has a distalmost end, and wherein the connection member has a proximal most end, and wherein the distalmost end of first bushing is proximal of the proximalmost end of the connection member.

2. The medical device of claim 1, further comprising an outer catheter having a proximal end region, a distal end region and a lumen extending therein, wherein the elongate member is configured to translate, rotate or both translate and rotate within at least a portion of the lumen of the outer catheter.

3. The medical device of claim 2, wherein the outer catheter includes an inner surface, and wherein the second outer surface of the first bushing is configured to shield the first outer surface of the connection member from contact with the inner surface of the outer catheter.

4. The medical device of claim 1, wherein the first bushing includes an aperture, and wherein the elongate member extends through the aperture.

5. The medical device of claim 1, wherein the first bushing is free to translate, rotate or both translate and rotate along the elongate member.

6. The medical device of claim 1, wherein the first bushing extends circumferentially around the outer surface of the elongate member.

7. The medical device of claim 1, wherein the first bushing directly contacts the connection member.

8. The medical device of claim 1, further comprising a second bushing, and wherein the first bushing is positioned proximal to the connection member and wherein the second bushing is positioned distal to the connection member.

9. The medical device of claim 8, wherein the second bushing includes a third outer diameter and wherein the third outer diameter is greater than the first outer diameter.

10. The medical device of claim 1, wherein the distal end region of the end effector includes a basket.

11. The medical device of claim 1, wherein the distal end region of the end effector includes a snare.

12. A medical device, comprising:
- a handle;
- an outer member coupled to the handle, the outer member having an inner surface and a lumen extending therein;
- a drive shaft extending within the lumen of the outer member, the drive shaft having a proximal shaft portion and a distal shaft portion;
- an end effector coupled to the distal shaft portion of the drive shaft; and
- a connection system configured to couple the proximal shaft portion of the drive shaft to the distal shaft portion of the drive shaft;
- wherein the connection system includes a connection member and a first bushing, the connection member coupled to an outer surface of the proximal shaft portion of the drive shaft and an outer surface of the distal shaft portion of the drive shaft, the connection member having a first outer diameter and an inner lumen, and wherein the first bushing has a second outer diameter larger than the first outer diameter, and wherein the first bushing is spaced away from the connection member along a longitudinal axis of the medical device;
- wherein the proximal shaft portion of the drive shaft extends within a portion of the inner lumen of the connection member, and wherein the distal shaft portion of the drive shaft extends within a portion of the inner lumen of the connection member;
- wherein the first bushing has a distalmost end, and wherein the connection member has a proximal most end, and wherein the distalmost end of first bushing is proximal of the proximal most end of the connection member.

13. The medical device of claim 12, wherein the first bushing is configured to space an outer surface of the connection member away from the inner surface of the outer member.

14. The medical device of claim 13, wherein the first bushing includes an aperture, and wherein the drive shaft extends through the aperture.

15. The medical device of claim 13, wherein the first bushing is directly attached to the drive shaft.

16. The medical device of claim 13, wherein the first bushing is free to translate, rotate or both translate and rotate along the drive shaft.

17. The medical device of claim 13, further comprising a second bushing, and wherein the first bushing is positioned proximal to the connection member and wherein the second bushing is positioned distal to the connection member.

* * * * *